United States Patent [19]
Iglesias

[11] 3,973,568
[45] Aug. 10, 1976

[54] STABILIZED CUTTING LOOP FOR RESECTOSCOPE WITH UNIMPAIRED VISION OF THE OPERATIVE FIELD

[76] Inventor: Jose J. Iglesias, 1341 North Ave., Elizabeth, N.J. 07200

[22] Filed: Feb. 12, 1975

[21] Appl. No.: 549,492

Related U.S. Application Data

[63] Continuation-in-part of Ser. No. 219,687, Jan. 21, 1972.

[52] U.S. Cl. .......................................... 128/303.15
[51] Int. Cl.² ......................................... A61B 17/32
[58] Field of Search ...................... 128/303.15, 4–8

[56] References Cited
UNITED STATES PATENTS

| 2,888,017 | 5/1959 | Wallace | 128/303.15 |
| 3,752,159 | 8/1973 | Wappler | 128/303.15 |
| 3,901,242 | 8/1975 | Storz | 128/303.15 |

FOREIGN PATENTS OR APPLICATIONS

| 1,548,389 | 10/1968 | France | 128/303.15 |

Primary Examiner—Robert W. Michell
Assistant Examiner—Lee S. Cohen
Attorney, Agent, or Firm—Scrivener Parker Scrivener and Clarke

[57] ABSTRACT

The cutting loop assembly forming part of resectoscope is stabilized, strengthened and reinforced by a tube which is slidably mounted on the distal end of the telescope tube and lies between the diverging and parallel arms of the cutting loop and which is shortened at its distal end so that it does not invade the field of vision of the operative field through the telescope tube when the cutting loop is at its maximum distal extension, and the connection of the stabilizing member to the parallel arms of the cutting loop is made by members which extend in a distal direction from the distal end of the stabilizing member, thus compensating for any reduction in the stabilizing and strengthening effect of the tube due to the reduction of its length.

4 Claims, 3 Drawing Figures

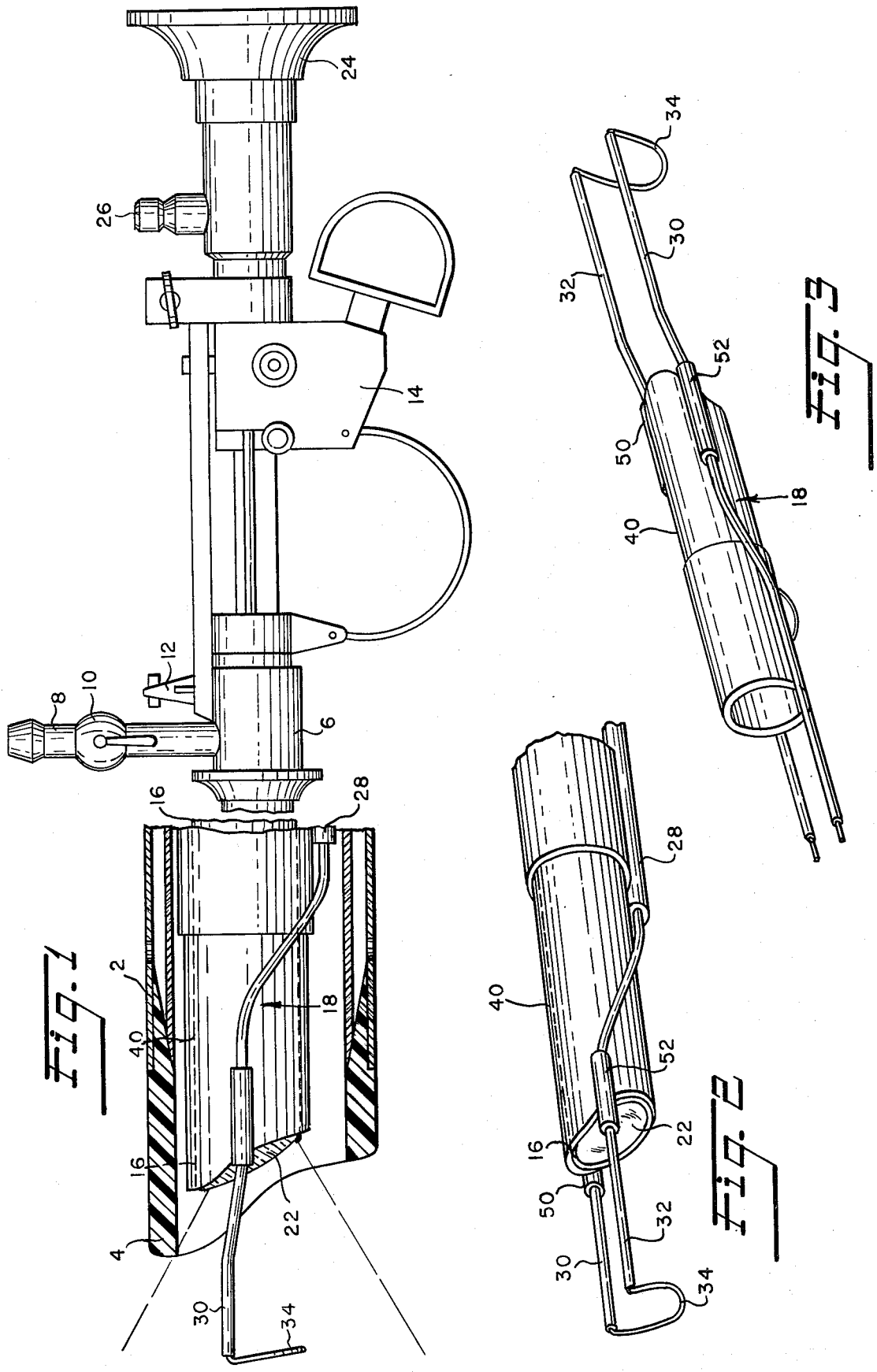

3,973,568

STABILIZED CUTTING LOOP FOR RESECTOSCOPE WITH UNIMPAIRED VISION OF THE OPERATIVE FIELD

RELATION TO OTHER CASES

This application is a continuation-in-part of my co-pending application Ser. No. 219,687, filed Jan. 21, 1972, for Stabilized Cutting Loop for Resectoscope.

DESCRIPTION OF THE DRAWINGS

FIG. 1 is a side elevational view of a resectoscope, being partially broken away and enlarged to illustrate the cutting loop assembly provided by the invention and its relation to other parts of the instrument, and FIGS. 2 and 3 are perspective views of two embodiments of the stabilized cutting loop assembly provided by the invention.

BACKGROUND OF THE INVENTION

A resectoscope having parts of conventional construction is disclosed in FIG. 1 as background for disclosure of the invention, and comprises the tubular sheath 2 which provides a passageway through the human urethra to the area of visual and operative interest, and which has a beak 4 at its distal end the shape of which is such that the side walls thereof recede in the proximate direction from the upper part of the distal end of the beak to the lower part. At its proximate end the sheath has a socket base 6 at which there is a tube 8 with stopcock 10 for the introduction of clear irrigating fluid, and a thumb screw 12 for attaching the sheath's socket to the working element 14 for activating the cutting loop assembly and electrode in performing an operation. Within the sheath are the telescope 16 and the cutting loop electrode assembly 18.

The telescope has an objective lens 22 at its distal end and an ocular lens (not shown) and eyepiece 24 at its proximal end. Light conductors (not shown) extend through the telescope from an external connection 26 to the distal end for providing illumination. The field of vision at the operative field with the objective lens positioned as shown in FIG. 1 is illustrated by the broken lines shown in that figure and its shape is that of a truncated cone with the truncated surface at the objective lens.

The cutting loop electrode assembly 18 disclosed in FIGS. 1 and 2 comprises the elongated hollow stem 28 from the distal end of which there protrude the two parallel arms 30, 32 which are insulated wires and which are connected at their distal ends by a depending semi-circular bare wire cutting loop 34 which is activated by high frequency electrical energy to resect pathological tissues and coagulate bleeding vessels. The stem 28 and arms 30, 32 transmit electrical energy and the reciprocating movement of the working element 14 to the cutting loop 34.

The cutting loop assembly of a resectoscope, consisting of spaced arms and depending cutting loop, is notoriously weak and frequently bends or departs from proper alignment with the sheath and telescope, this occurring particularly in procedures involving lithiasis and carcinoma of the prostate. In addition to the possible adverse effects this may have on the operation being performed, the telescope and other parts of the resectoscope may be damaged or ruined by arcing or short-circuiting of the electrically charged loop.

In my co-pending application which is identified above I have disclosed and claimed means for stabilizing the cutting loop assembly by the interposition between the arms of the loop of a tube (see the definition of this word hereinafter) which extends between and is connected to the upwardly extending and diverging arms and the spaced parallel arms of the cutting loop assembly in order to stabilize the entire assembly. This stabilizing tube surrounds the distal end of the telescope tube and slidably moves along the telescope tube as the cutting loop is operated during a surgical procedure.

During such a procedure it is most important that the field of vision not be reduced or otherwise impaired, and this adverse effect can result from the movement of the distal end of the stabilizing tube into the field of vision through the telescope. In the most modern instruments the new telescope with rod lens has a wider field of endoscopic vision, and it has been found that the fenestra and the insulated arms of the cutting loop come into and interfere with the field of vision as the cutting loop is extended in performing a TUR procedure. In order to prevent this interference with the field of vision it has been proposed to shorten the fenestra, but I have found that this results in arcing between the bare wire cutting loop and the distal end of the telescope, which is not only most undesirable during an operative procedure but also damages the telescope, which is the most expensive and important part of the instrument. By the present invention I have provided means for preventing such impairment of the field of vision at the same time providing maximum stabilization of the cutting loop assembly consistent with lack of interference with the field of vision.

SUMMARY OF THE INVENTION

The tube which stabilizes the cutting loop is shortened at its distal end so that that end is proximate to the objective lens of the telescope when the cutting loop is fully extended, thereby providing an unimpaired field of vision, and the connection of the stabilizing tube to the arms of the cutting loop is made by means which extend in the distal direction from the distal end of the stabilizing tube, thereby providing maximum possible stabilization consistent with the reduced length of the distal end of the stabilizing tube.

DESCRIPTION OF THE INVENTION

The numeral 40 designates the tube disposed between and connected to the upwardly extending and diverging sections and the spaced parallel sections 30, 32 of the arms of the cutting loop assembly to stabilize and strengthen the assembly, as more particularly described and claimed in my co-pending application referred to above and in Wappler U.S. Pat. No. 3,752,159. As used in this specification and claims the word "tube" means, and shall be construed to mean, an elongated hollow body of any cross-sectional shape which is formed by a closed peripheral wall, as shown in the drawings forming part of this specification, or is part-tubular as disclosed in my application Ser. No. 219,687 and in the Wappler patent, or which is a complete tube throughout part of its length and part-tubular throughout part of its length as disclosed in my U.S. Pat. No. 3,856,015.

The stabilizing tube 40 is connected adjacent its proximate end to the distal end of stem 28 and surrounds and is slidably mounted on the stem of the telescope at and adjacent the distal end thereof, and extends between and is connected to the arms 30, 32 of the loop and moves with the loop, and therefore moves along the telescope tube with respect to the objective lens 22. In accordance with the invention the distal end of the tube 40 is proximate to the objective lens when the cutting loop electrode assembly is in its fully extended position in the direction of the operative field, although it may be closely adjacent the lens as shown in FIG. 1. As also shown in FIG. 1 the distal end of tube 40 may be beaked or otherwise shaped to conform to the configuration of the beak of the sheath and the distal end of the telescope tube.

This positioning of the distal end of the tube 40 requires, in practice, a reduction in the length of the tube and this, in turn, reduces the stabilizing and strengthening effect of the tube on the cutting loop assembly. In order to correct and compensate for this deleterious effect the invention provides means for increasing the stabilizing and strengthening effect of the shortened tube 40. Such means comprise the two tubes 50, 52 which are attached to the exterior wall of tube 40 adjacent the distal end thereof, which are spaced 180° apart, which engage and preferably surround the spaced parallel arms 30, 32 of the cutting loop assembly, and which extend in parallelism to each other beyond the distal end of tube 40 with their distal ends substantially distal to the distal end of tube 40. These tubes extend the stabilizing and strengthening effect of the tube 40 in a distal direction along the cutting loop assembly thus increasing that effect due to the tube itself. The tubes 50, 52 may be closed tubes or open-sided clips and may be of any cross sectional shape all of which are embodiments included in the word tube as applied to the parts 50, 52.

While the cutting loop electrode assembly specifically illustrated in FIGS. 1 and 2 and described in this specification is of the type having an elongated hollow stem 28 through which the electrically conductive wire extends, it will be understood that the invention is not limited to an assembly of that type or to any other type of assembly, and a second embodiment in which two wires extend along the telescope tube and support the cutting electrode at their distal ends is disclosed in FIG. 3 of the drawings.

I claim:

1. In a resectoscope, a tubular sheath having a distal end, an optical telescope having a tubular stem within the sheath having a distal end and having an objective lens adjacent the distal end of the sheath which defines a field of vision at the distal end of the telescope stem, a cutting loop assembly comprising
   a. at least one electrode wire carried by and mounted for reciprocation along the telescope stem and having a generally loop-shaped distal part comprising a pair of electrically insulated arms extending in spaced relation along opposite sides of the telescope stem and an uninsulated cutting electrode constituting a distal continuation of each arm and positioned in the field of vision of the telescope,
   b. a stabilizing tube slidably mounted on the telescope stem having a distal end adjacent the distal end of the sheath and extending between and engaging and supporting said spaced arms and maintaining the same in spaced relation to opposite sides of the telescope stem,
   c. the tube being of such length and so positioned with respect to the other parts of the resectoscope that its distal end is adjacent and proximate to the objective lens and does not extend into the field of vision of the telescope at the maximum extension of the cutting loop assembly in the direction of the operative field,
   d. and a connection between the distal end of the tube and each of the spaced arms.

2. The combination according to claim 1, in which two tubes provide the connection between the spaced arms and the stabilizing tube, the two tubes being connected respectively to the opposite exterior sides of the stabilizing tube and extending therefrom in a direction distal to the distal end of the stabilizing tube and which are connected respectively to the spaced arms.

3. The resectoscope according to claim 1, in which the electrode wire of the cutting loop assembly comprises two parallel wires extending along and parallel to the telescope stem.

4. The resectoscope according to claim 1, comprising in addition a tubular body carried by and reciprocable along the telescope stem through which the electrode wire extends and from which it is electrically insulated.

* * * * *